(12) United States Patent
Sumikawa et al.

(10) Patent No.: US 7,081,474 B2
(45) Date of Patent: *Jul. 25, 2006

(54) DRUGS TO IMPROVE SYNAPTIC TRANSMISSION

(75) Inventors: Katumi Sumikawa, Irvine, CA (US); Ken-Ichi Ito, Yamagata (JP); James L. McGaugh, Newport Beach, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/806,953

(22) Filed: Mar. 22, 2004

(65) Prior Publication Data

US 2004/0242553 A1    Dec. 2, 2004

Related U.S. Application Data

(63) Continuation of application No. 08/756,930, filed on Dec. 2, 1996, now Pat. No. 6,710,073, which is a continuation of application No. 08/309,871, filed on Sep. 20, 1994, now abandoned.

(51) Int. Cl.
  *A61K 31/35* (2006.01)
(52) U.S. Cl. ..................... 514/450; 549/269
(58) Field of Classification Search .............. 514/450; 549/269, 270
  See application file for complete search history.

(56) References Cited

U.S. PATENT DOCUMENTS

| 5,214,039 A | 5/1993 | Kawaguchi et al. |
| 5,242,932 A | 9/1993 | Gandy et al. |

FOREIGN PATENT DOCUMENTS

| DE | 3247379 | 6/1984 |
| DE | 4305249 | 8/1994 |
| EP | 0230967 | 8/1987 |
| JP | 57159710 | 10/1982 |

OTHER PUBLICATIONS

Boast and Abou-Gharbia, Immune-Directed Mechanisms in Alzheimer's Disease, DN&P, 6(7):564, 1993.
N.R. Carlson, Foundationsl of Physiological Psychology, "Chapter 12: Learning and Memory," 2nd Edition, Allyn & Bacon: Boston, 1992, pp. 421-430.
Caporaso, et al., Morphologic and Biochemical Analysis of the Intracellular Trafficking of the Alzheimer beta/A4 Amyloid Precursor Protein, Journal of Neuroscience, 14(5 Pt 2):3122, May 1994.
Caporaso, et al., Protein Phosphorylation Regulates the Cellular Trafficking and Processing of the Alzheimer Beta/A4 Amyloid Precursor Protein, Molecular Mechanisms of Membrane Traffic, NATO ASI Series, vol. H74, 1993.
Caporaso, et al., Chloroquine Inhibits Intracellular Degradation But Not Secretion of Alzheimer beta/A4 Amyloid Precursor Protein, Proceedings of the National Academy of Sciences of the U.S., 89(6):2252, Apr. 5, 1992.
Dyrks, et al., Generation of βA4 from the amyloid protein precursor and fragments thereof, FEBS 13297, 335(1):89, 1993.
Carol Ezzell, "Neuroscientists Lay The Groundwork for Détente In the Battle of Learning and Memory Research", The Jrnl. Of NIH Research, 4:60-64, Nov. 1992.
Gabuzada, D., et al., Inhibition of Energy Metabolism Alters the Processing of Amyloid Precursor Protein and Induces a Potentially Amyloidogenic Derivative, Journal of Biological Chemistry, 269(18):13623-8, May 6, 1994.
Gourmelon, et al., "Action of 1,4-diacid anydrides on m-disubsituted aromatic compounds, (Abstract No. 135556d, XP002035950)",. Chemical Abstracts 81(21) (Nov. 25, 1974).
Haass, et al., β-Amyloid Peptide and a 3-kDa Fragment are Derived by Distinct Cellular Mechanisms, J. Biol. Chem., 268(5):3021, 1993.
Haass, et al., Normal Cellular Processing of a beta-Amyloid Precursor Protein Results in the Secretion of the Ayloid beta peptide and Related Molecules, Annals of the N.Y. Acad. of Sciences, 695:109-116, Sep. 24, 1993.
Rachel Nowak, "Corners of the Mind: The Cellular Basis of Memory and Learning," The Jrnl. Of NIH Research, 4:49-55, Jan. 1992.
Nguyen et al., Requirement of a Critical Period of Transcription for Induction of a Late Phase of LTP, Science, 265:1104-1107, Aug. 19, 1994.
Rockefeller University, "APP Modulators for the Treatment of Amyloidosis", Curr. Opin. Ther. Pat., 4/1:77, 1994.
Takashi, et al., "Ascotoxin" (Abstract No. 71697n, XP002045314)., Chemical Abstracts 76(13) (Mar. 27, 1972).

*Primary Examiner*—Amelia A. Owens
(74) *Attorney, Agent, or Firm*—Morrison & Foerster LLP

(57) ABSTRACT

Peripherally administered Brefeldin A and its analogs and derivatives are used to enhance learning and reverse memory dysfunction through induced long term potentiation in hippocampal issues.

12 Claims, 9 Drawing Sheets

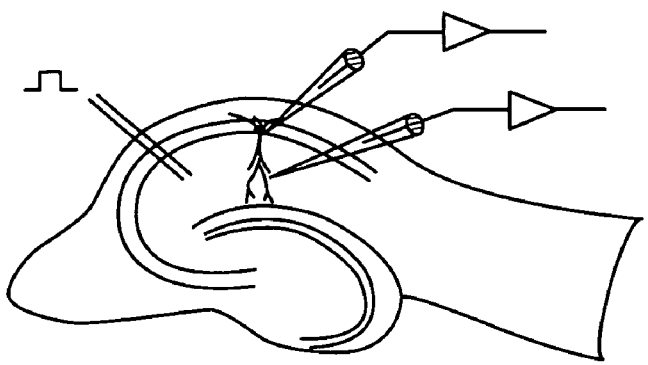
FIG. 1A
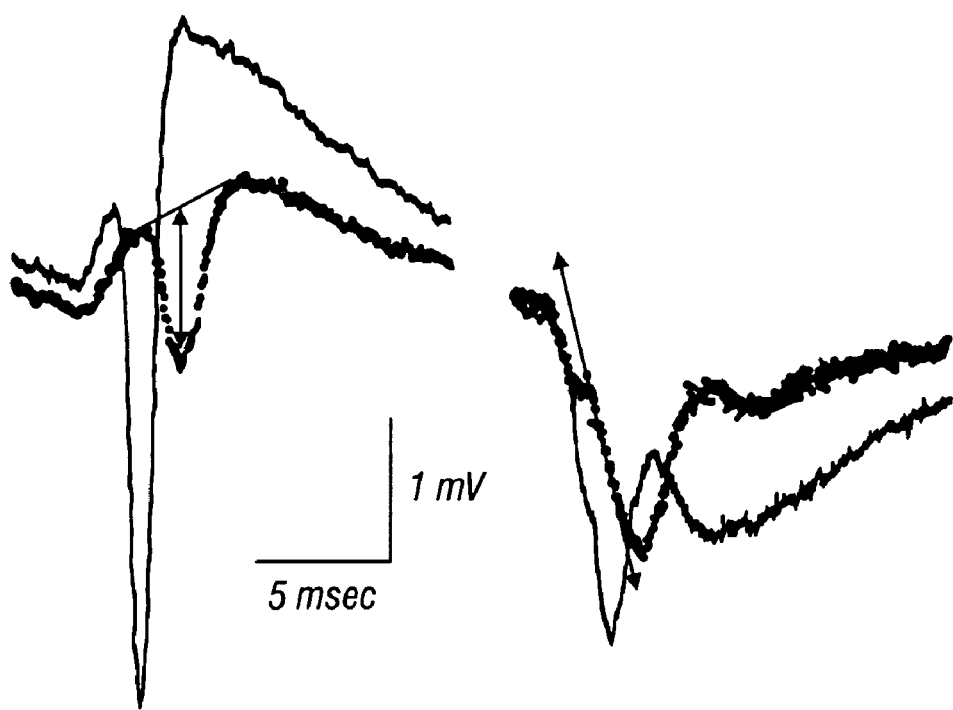
FIG. 1B  FIG. 1C

Dose-response curve for BA administered 2hr pre-training in the inhibitory avoidance task. Animals tested at 48hr. N=12 mice/group.

Dose-response curve for BA administered 2hours pre-training in the inhibitory avoidance task. Animals tested at 48 hours. N=12 mice/group.

Dose-response curve (Pooled Data) for BA given 2 hours pre-training on the Y maze task. Errors on reversal tested at 48 hours. N=12 mice/group.

Time curve for injections of BA(3MG/KG) in animals tested in the inhibitory avoidance task. Animals tested at 48 hours N=12 mice/group.

Time course for injections of BA(3MG/KG) at different time points before testing on Y maze reversal discrimination task. N=12 mice/group.

DRUGS TO IMPROVE SYNAPTIC TRANSMISSION

CROSS REFERENCE TO RELATED APPLICATIONS

This application is a continuation (and claims the benefit of priority under 35 USC 120) of U.S. application Ser. No. 08/756,930, filed Dec. 2, 1996 now U.S. Pat. No. 6,710,073, which is a continuation and claims priority to U.S. application Ser. No. 08/309,871 filed Sep. 20, 1994 now abandoned. The disclosure of the prior applications are considered part of (and are incorporated by reference in) the disclosure of this application.

STATEMENT REGARDING FEDERALLY SPONSORED RESEARCH

This invention was made with Government support under Grant Nos. NS25928 and NS27341, awarded by the National Institutes of Health. The Government has certain rights n this invention.

BACKGROUND OF THE INVENTION

1. Field of the Invention

This invention relates to drugs for enhancing learning potential and to methods of their use for improving learning capacity. More particularly, this invention relates to drugs that induce long term potentiation (LTP) and enhance cognitive function in mammals.

2. Description of Related Art

The hippocampal formation, which is a specialized region of the limbic cortex located in the temporal lobe, is also known as the comu ammonis from which come the names of its two major divisions, CA1 and CA3. Neurons in the entorhinal cortex relay incoming information through a bundle of axons called the perforant path to neurons in the dentate gyrus, another region of the hippocampal formation. All association areas of the brain send information to, and receive information from, the hippocampal formation, via the entorhinal cortex. Thus, the hippocampal formation is in a position to know—and to influence—what is going on in the rest of the brain. Several neurotransmitters, including glutamate, gamma-aminobutyric acid (GABA), noradrenalin, serotonin, and acetylcholine have a profound effect on the activity of the hippocampal formation and, undoubtedly, on its functions.

LTP is a use-induced increase in the magnitude of the postsynaptic response (i.e., the strengthening of the synaptic connection between two neurons) caused by binding of glutamate to receptors in the postsynaptic membrane. However, the maintenance of LTP may involve both presynaptic and postsynaptic mechanisms (for review, see Bliss & Collingridge, *Nature*, 361:31–39, 1993). This increase is understood to signify that LTP is associated with enhanced cognitive function. LTP was first discovered in 1966 to result from a response to high frequency electrical stimulation (tetanus) of the axons in the perforant path with a burst of approximately one hundred pulses of electrical stimulation, delivered within a few seconds. Evidence that LTP has occurred is obtained by periodically delivering single pulses to the perforant path and recording the response in the dentate gyrus. If, for example, the population EPSP is larger than it was before tetanus, LTP has taken place. LTP can also be produced in fields CA3 and CA1 as well as in the neocortex (Perkins and Teyler, *Brain Research*, 439:25–47, 1988; Brown, et al., in *Neural Models of Plasticity: Experimental and Theoretical Approaches*, ed. J. H. Byrne and W. O. Berry, San Diego: Academic Press 1989). It can last for several months (Bliss and Lømo, *J. Physiol.*, 232:331, 1973). Even more importantly, LTP can involve the interaction between different synapses on a particular neuron. That is, when weak and strong synapses on a single neuron are stimulated at approximately the same time, the weak synapse becomes strengthened, and this strengthening of the synapse has been proposed to be the basis of long-term learning (Hebb, *The Organization of Behavior*, New York: Wiley-Interscience, 1949). This phenomenon, produced by the association (in time) between the activity of two synapses, is called associative LTP because it resembles what happens during classical conditioning for learned responses.

Many experiments have demonstrated that associative LTP can take place in hippocampal tissue slices, which are maintained in a temperature-controlled chamber filled with a liquid that resembles interstitial fluid and remain alive for up to 40 hours. For example, Chatterji, Stanton, and Sejnowski (*Brain Research*, 95:145–150, 1989) stimulated two sets of axons: the axons that connect the dentate gyrus with field CA3 (strong input) and a set of collateral axons arising from other pyramidal cells in CA3 (weak input). The researchers found that when the weak input and the strong input were stimulated together, the response of the CA3 pyramidal cells to the weak input increased. LTP occurs when a sufficient amount of calcium enters the post-synaptic neuron. When a hippocampal slice is placed in a solution that contains very little calcium, LTP does not take place (Dunwiddie and Lynch, *Brain Res.*, 169:103–110, 1979). It was found that induction of LTP could be blocked by the intracellular injection of the calcium chelator (EDTA) (Lynch, et al., *Nature*, 305:719–721, 1983). These results suggested that calcium signaling is involved in the induction of LTP Several calcium-sensitive enzymes have been proposed to play a role in converting the initial calcium signal into persistent modifications of synaptic strength. For example, entry of calcium into the dendritic spine causes structural changes in the spine by activation of the enzyme calpain, which is instrumental in break-down of spectrin, a protein that appears to serve as a framework support for the structure of the spine. These changes decrease the electrical resistance between the spine and the rest of the dendrite, thus increasing the effect of EPSPs on the dendritic membrane potential. Staubli, et al. (*Brain Res.*, 444:153–158, 1988) found that proteolytic activity of calpain is blocked by infusion of a drug called leupeptin into lateral ventricles of rats with the result that electrical stimulation of the hippocampus no longer produces LTP.

Some sort of additive effect is required to produce LTP. A series of electrical pulses delivered at a high rate all in one burst will produce LTP, but the same number of pulses given at a slow rate will not. Apparently, each pulse produces an aftereffect that dissipates with time. If the next pulse comes before the aftereffect fades away, its own effect will be amplified. Thus, each pulse "primes" the following one. If the interval between pulses is chosen carefully, very little stimulation is required.

Experiments have shown that the priming effect consists of a depolarization of the postsynaptic membrane: the depolarization caused by one pulse primes the synapse for the next one. The N-methyl-D-aspartate (NMDA) receptor, a type of glutamate receptor named for its agonist, are glutamate activated calcium permeable ion channels, which are normally blocked by magnesium ions to prevent calcium ions from entering the cell. When the postsynaptic membrane is depolarized the magnesium ion is ejected from the ion channel, and in the presence of glutamate, the channels will open, allowing calcium ions to enter the dendritic spine where they effect the physical changes responsible for LTP. Collingridge, et al. (*J. Physiol.*, 334:33–46, 1983) discovered that drugs, such as APV (2-amino-5-phosphonopentanoate), that block N-methyl-D-aspartate (NMDA) receptors prevent LTP from taking place in the CA1 field and the dentate gyrus. However, such drugs had no effect on any LTP that had already been established, indicating that the NMDA receptor is not involved in the maintenance of LTP.

While LTP is a strong cellular model for learning and memory, whether LTP participates in memory formation is still unresolved. In general, treatments that affect LTP also have consequences for the acquisition of certain learning tasks. When rats are exposed to novel, complex environments, the extracellular population spike in the dentate gyrus increases, just as it does when the entorhinal cortex is subjected to high-frequency stimulation, and treatments that interfere with LTP also interfere with the learning of tasks in which the hippocampus is involved. For instance Morris, et al. (*Nature*, 319:774–776, 1986) trained rats in manoeuvreing a "milk maze", a spatially guided task in separate experiments. When APV was infused into the animals' lateral ventricles, the animals were prevented from learning the task. Physical damage to the hippocampus results in the same inability to learn a spatially guided task. Perhaps the strongest support for a role for LTP in learning and memory will come from the discovery of a drug that induces LTP in vivo and enhances at least one form of learning in mammals.

Heretofore, no drug has been discovered that will chemically stimulate the hippocampus so as to cause LTP in vivo when administered peripherally. Drugs that induce LTP may be effective in the treatment of cognitive impairment such as memory loss and learning dysfunction associated with Alzheimer's Disease, stroke and other neurological disorders. They may also be useful for enhancing learning potential in the healthy mammalian brain. The practical utility of such a drug will depend upon its ability to cross the blood-brain barrier without inducing deleterious effects, such as seizures and convulsions, since injection into the lateral ventricals of the brain is not a practical method of enhancing learning in humans and animals. Brief application in vitro to slices of rat hippocampus of $K^+$ channel blockers (tetraethylammonium, mast-cell-degranulating peptide) or the metabotropic glutamate receptor agonist aminocyclopentane-1S,3R-decarboxylate (1S,3R-ACPD) induces a long lasting potentiation of synaptic responses (Cherubini, et al., *Nature*, 328:70–73, 1987; Aniksztejn and Ben-Ari, *Nature*, 349:67–69, 1991; and Bashir, et al., *Nature*, 363: 347–350, 1993). However, when mast-cell-degranulating peptide or 1S,3R-ACPD are administered directly into the brain, both compounds produce seizures and convulsions in experimental animals (Cherubini, et al., *Nature*, 328:70–73, 1987; Bidard, et al., *Brain Res.*, 48:235–244, 1987; Sacaan and Schoepp, *Neurosci. Lett.*, 139:77–82, 1992). Therefore, the need exists for the discovery of new compounds capable of inducing LTP in vivo and for methods of utilizing them so as to enhance learning ability in humans and animals.

SUMMARY OF THE INVENTION

Novel compounds, such as analogs and derivatives of Brefeldin A (BA), are provided that safely induce LTP and enhance cognitive function when administered peripherally to a mammal. These compounds cross the blood-brain barrier and increase the efficiency of synaptic transmission in the hippocampus region of the brain to induce LTP Heretofore, all compounds that induce LTP in vitro and have been tested for in vivo induction of LTP have caused seizures and convulsions in laboratory animals. By contrast, the compounds of this invention can be safely administered in vivo to mammals without inducing ill effects in the subject treated.

Methods are provided for using compounds such as BA and analogs and derivatives of BA to enhance learning and memory storage in subjects with healthy brains wishing to perform at a higher learning level as well as in subjects suffering from learning and memory dysfunction associated with a decrease in the efficiency of synaptic transmission or loss of functioning synapses such as is found in the early stages of Alzheimer's disease.

BRIEF DESCRIPTION OF THE DRAWINGS

FIG. 1A is a schematic diagram showing positions of stimulation and recording electrodes in a hippocampal slice. Recording electrodes were placed in the pyramidal cell layer of CA1 region and the stratum radiatum for extracellular recordings of the population spike (PS) and field excitatory postsynaptic potential (EPSP), respectively. The experiments were carried out with over 30 slices.

FIG. 1B is a graph showing the PS recorded in a slice of hippocampal tissue before (dotted line) and 150 minutes after (solid line) application of BA. The PS amplitude increases 150 minutes after application of BA.

FIG. 1C is a graph showing field EPSPs recorded in a slice of hippocampal tissue before (dotted line) and 150 minutes after (solid line) application of BA. The amplitude and slope of field EPSP increase 150 minutes after application of BA.

A DETAILED DESCRIPTION OF THE INVENTION

Figure 2A:
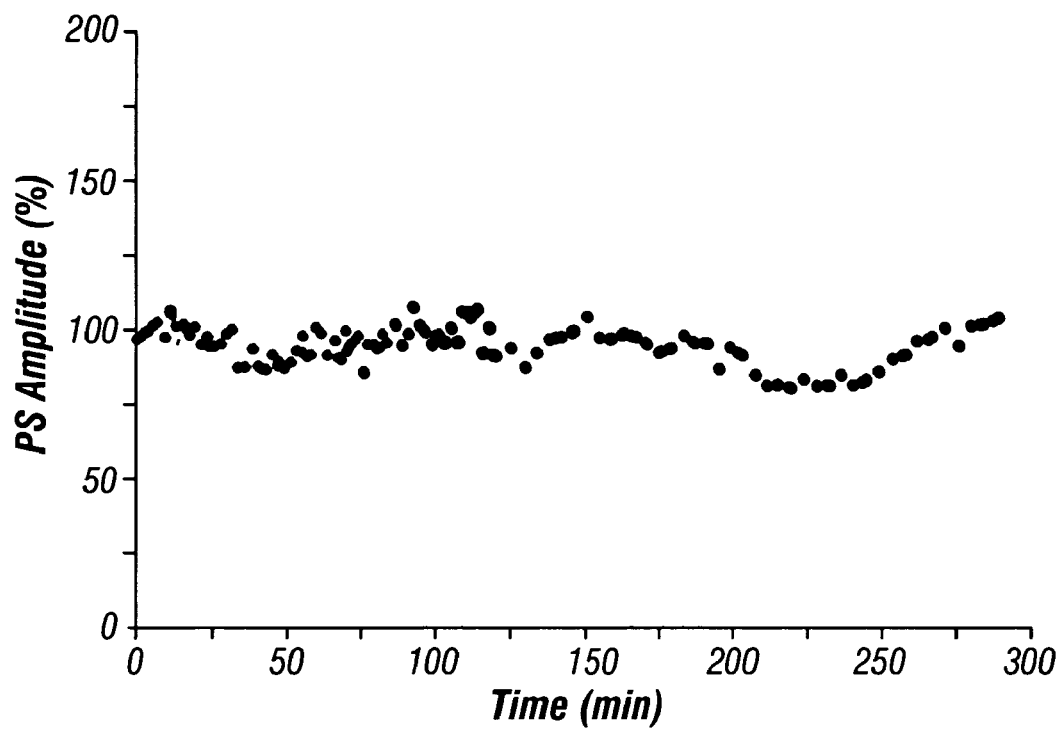
FIG. 2A is a graph showing the time course of the changes in amplitude of the PS recorded in a control hippocampal slice exposed to vehicle solution without BA. Fluctuations of PS amplitude were within ±20% of baseline during the recording. The PS amplitude was measured as indicated by the arrow in FIG. 1B.

The present invention provides compounds that cross the blood brain barrier when administered peripherally, which increase the efficiency of synaptic transmission in the hippocampal region of the brain. Such compounds increase LTP of such synapses without involving NMDA receptors. They have utility for enhancing learning and memory storage in mammalian subjects with healthy brains as well as in subjects suffering from learning and memory dysfunction due to a decrease in the efficiency of synaptic transmission or loss of functioning synapses as occurs in Alzheimer's disease.

The preferred compounds are BA and analogs or derivatives thereof, which produce significant dose and time-dependent effects on memory in learning tasks. Performance in retention tasks is also enhanced in animals that were administered the drugs as much as two hours after learning of the task was terminated, indicating that the effects of the drug are not due to influences on non-associational processes, such as sensory, motivational and motor processes, that might directly affect acquisition or retention of learning.

Derivatives and analogs of BA are screened and monitored to determine their usefulness in inducing LTP using utilizing hippocampal slice preparations. A bipolar stimulation electrode is positioned in the stratum radiatum to stimulate Schaffer collateral/commissural fibers. Recording electrodes are placed in the pyramidal cell layer of the CA1 region and in the stratum radiatum as shown in FIG. 1A to record the population spike (PS) and field excitatory postsynaptic potential (EPSP), respectively. PS are recorded before administration of the drug to be tested and at timed intervals after administration of the drug, for instance at about 2 minute intervals for up to 250 minutes after administration of BA in artificial cerebrospinal fluid at a concentration of 0.1 µg/ml. To evaluate the effect of BA, control slices of hippocampal tissue were tested with vehicle. In addition, the slope of the field EPSP is monitored as an indication of induction of LTP as illustrated in FIG. 1C.

The chemical structure of BA is as follows:

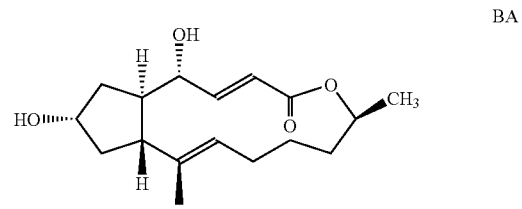

As used herein the term "derivatives and analogs of BA" are those compounds that produce at least 50% of the population spike or field excitatory postsynaptic potential in slices of hippocampal tissue generated by administration of BA. Preferred compounds have the chemical formula I or II:

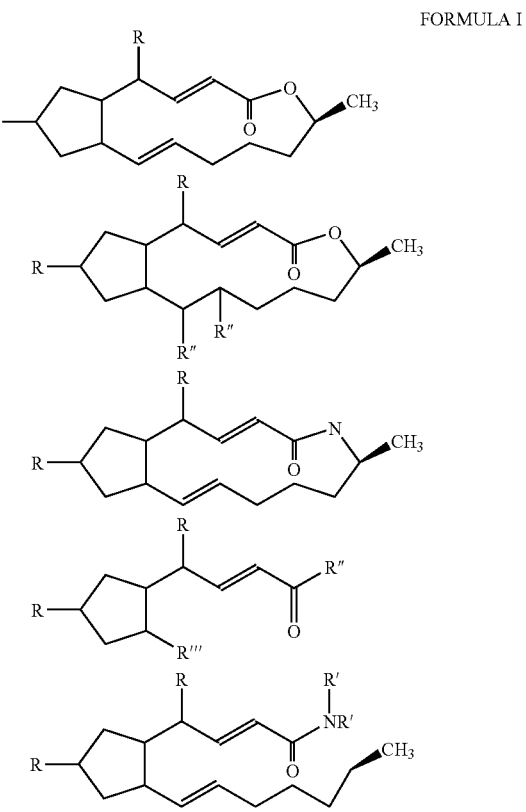

FORMULA I

-continued

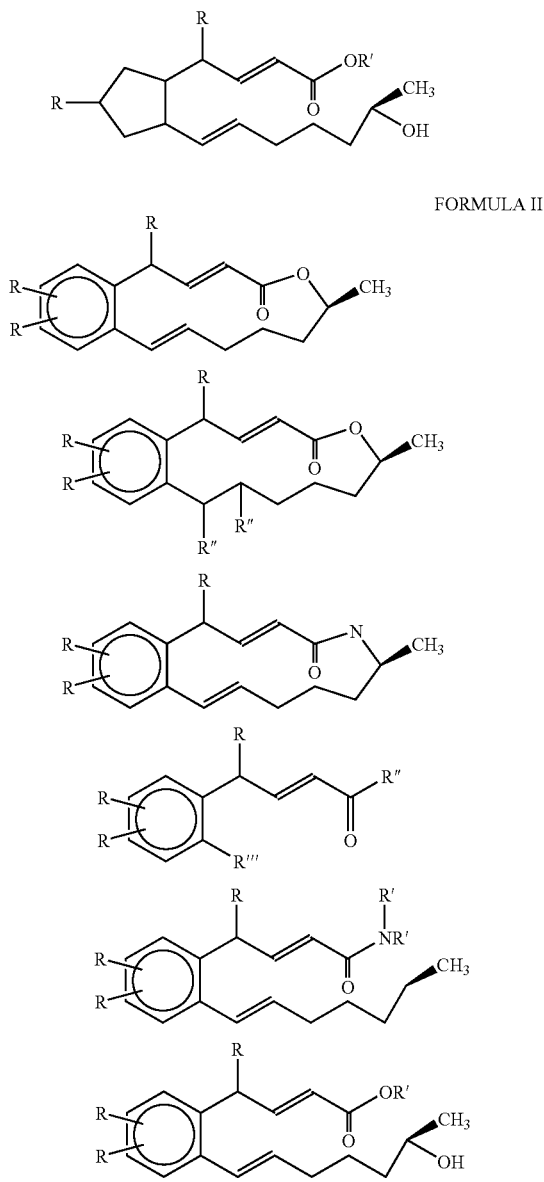

FORMULA II wherein each R is independently selected from —OH, —OR¹, —SH, —SR¹, —NR²R², and a carbonyl oxygen; each R' is independently a $C_1$ to $C_4$ alkyl; each R" is independently selected from hydrogen, —OH, —OR¹, and —NR²R²; wherein R'" is independently selected from —CHO, —COOH,

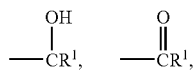

and —CONR²R²; and R* is hydrogen or —OH; and wherein R¹ is a $C_1$ to $C_4$ alkyl; and R² is hydrogen or a $C_1$ to $C_4$ alkyl.

The novel compounds of this invention have the chemical formula:

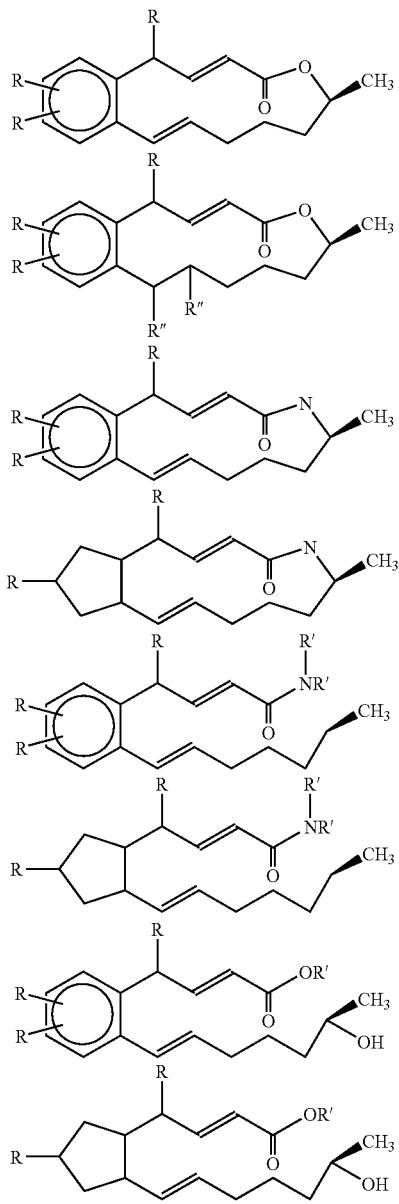

wherein each R is independently selected from —OH, —OR¹, —SH, —SR¹, —NR²R², and a carbonyl oxygen; each R' is independently a $C_1$ to $C_4$ alkyl; each R" is independently selected from hydrogen, —OH, —OR¹, and —NR²R²; wherein R'" is independently selected from —CHO, —COOH,

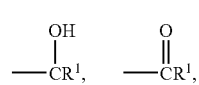

and —CONR²R²; and R* is hydrogen or —OH; and wherein R¹ is a $C_1$ to $C_4$ alkyl; and R² is hydrogen or a $C_1$ to $C_4$ alkyl.

Methods for synthesis of BA and its derivatives and analogs are well known in the art (Corey and Wollenberg, *Tetrahedron Lett.*, pp.4701–4704, 1976; Kitahara, et al., *Tetrahedron Lett.*, pp.3021–3024, 1979).

In behavioral experiments using mice, evidence has been obtained indicating that BA enhances retention in two learning tasks: inhibitory avoidance (IA) and Y maze discrimination (YMD). When administered peripherally by intraperitoneal injection two hours before training, the drug produced dose-dependent effects on retention tests administered 48 hours after training. In both tasks significant effects were obtained at doses of 1.0 and 3.0 mg/kg but a dose of 10 mg/kg was most effective in the Y maze task. Furthermore, in both tasks, the drug was also effective in enhancing retention when injected either one week prior to training or immediately post-training. In the Y maze task significant effects were obtained when the drug was administered two hours, but not six hours after training. Drug injections administered two hours post-training were ineffective in the IA task.

Thus, the evidence clearly indicates that BA produces significant dose and time-dependent effects in mammals on 48 hour memory in learning tasks. The fact that retention is enhanced by post-training injections indicates that the drug effects are not due to influences on non-associational processes (e.g. sensory, motivational and motor processes) directly affecting acquisition or retention performance. Consequently, the findings indicate that the drug affects retention by altering memory storage processes. The memory enhancing effects obtained with BA are similar to those obtained with drugs affecting noradrenergic agonists, opiate and GABAergic antagonists, as well as cholinergic agonists.

The two tasks used in the experiments described in this application provide very different measures of memory. In the IA task, mice indicated memory of footshock training by inhibiting a high probability response (leaving a lighted compartment of an alley to enter a darkened compartment). In the Y maze task, on the other hand, mice indicated memory of training on how to escape footshock even though entrances to the escape alley had been punished with footshock during retention test trials. Thus, the two behavioral measures, response inhibition and alley choice, provide evidence that drug injections administered either before or shortly after training significantly improved memory on retention as assessed two days after training.

LTP induced by BA differs in several ways from that produced by other art methods utilizing a train of high-frequency electrical stimulations. First, electrical stimulations induce LTP immediately, whereas induction of LTP by BA usually occurs 60 to 120 minutes after drug application. Second, in the case of tetanus-induced LTP, activation of the NMDA receptor is essential for triggering LTP In contrast, induction of LTP by BA appears to be by a process independent of NMDA receptors because BA causes LTP in the presence of an inhibitor of NMDA receptors known as 2-amino-5-phosphonopentanoate (APV).

BA induces LTP in the CA1 area of the hippocampus of anesthetized rats after peripheral administration, indicating that BA crosses the blood-brain barrier and acts on target molecules in the brain that lead to induction of LTP. This observed action of BA is novel.

There is evidence to suggest that synthesis of new proteins is necessary for LTP. Expression of the immediate early genes zif/268 and c-fos is induced by tetanic stimulation, and is blocked by NMDA receptor antagonists. These results indicate that calcium signalling is required for the induction of immediate early genes. Furthermore, after tetanization, protein kinase C mRNA is down regulated, whereas mRNA encoding $Ca^{2+}$/calmodium-dependent protein kinase is up-regulated. Thus, altered gene expression may play a role in induction, expression and/or maintenance of LTP. Using in situ and Northern blot hybridization techniques, the effects of BA on the expression of genes (immediate-early genes, growth factor genes, neuroactive peptide genes, protein kinase genes, and receptor and ion channel genes) can be measured in specific brain regions. It can be determined whether detected changes in gene expression are accompanied by changes in levels of encoded protein by using antibodies to the protein encoded by the gene of interest.

Neurotransmitter receptors and ion channels are fundamental elements required for signaling in the brain. In particular, the involvement of several neurotransmitter receptors in the induction of LTP by a train of high-frequency electrical stimulations has been demonstrated by the use of receptor antagonists. Through its action on such molecules, BA affects signal transduction processes involved in LTP. Thus, by expression of a variety of receptors and ion channels in Xenopus oocytes or cultured cells, and by using a variety of biochemical and electrophysiological techniques, it can be determined whether binding of BA modulates the function of a receptor (for example, glutamate, acetylcholine, or GABA receptors) or an ion channel (for example sodium, potassium or calcium ion channels), or whether it activates second messenger pathways. Since many different subtypes of receptors and ion channels have already been cloned, a cDNA coding for a specific subtype of a particular receptor or ion channel can be obtained relatively easily utilizing the polymerase chain reaction in standard techniques. Receptor cDNAs can be expressed in cultured cells for studying the interaction of the receptors or ion channels with BA with standard electrophysiological techniques.

To determine the drug binding protein, conventional techniques for characterization of drug binding proteins known to one of skill in the art can be used. These techniques involve first the purification of the desired protein by monitoring the binding activity of radioactive drugs in fractions of broken cell preparations after each purification step. In an alternative embodiment, the gene expressing the protein sequence to which BA binds is determined by preparation of a cDNA library in an RNA expression vector from size-fractionated hippocampus mRNA, and an mRNA mixture is synthesized in vitro and assayed after injection into oocytes using a well known technique described by J. B. Gurdon, et al. (*Nature*, 233:177–82, 1971) and Sumikawa, et al. (*Methods in Neuroscience*, Vol 1, 30–45, 1989). The expression of BA binding protein is then tested by measurement of electrophysiological responses or $Ca^{2+}$ signals in response to application of BA in vitro. When a positive response is observed, the library is subdivided serially until a single positive clone is identified. From the clone, the BA binding protein can be obtained and reproduced either synthetically or recombinantly using techniques well known in the art. Resolution of the structure of the binding protein allows for the designing and screening of new drugs.

One embodiment of this invention is a method for enhancing synaptic efficacy by inducing LTP in subjects by peripheral administration of a therapeutic amount of the compounds of this invention, such as BA and its analogs and derivatives. Another embodiment of this invention is a method for ameliorating learning deficiencies in a subject in need thereof by peripheral administration of a therapeutic amount of a compound of this invention. About 5% of the general population over the age of 65 suffer from Alzheimer's disease, and the prevalence of this disease increases with increasing aging. The progressive aging of our population means that more people are likely to suffer from Alzheimer's disease. There is no effective treatment for Alzheimer's disease. Thus, development of treatments for this disease is an important issue. Synaptic connections in the hippocampus, a brain region known to be important for learning and memory, are especially vulnerable to Alzheimer's disease, a fact presumed to account for the loss of memory characteristic of early stages of Alzheimer's disease. Therefore, one method for reducing the memory loss associated with Alzheimer's disease is to enhance synaptic efficacy at synapses remaining on the slowly atrophying neurons by peripheral injection of a therapeutic amount of a compound of this invention.

Yet another embodiment of this invention is a method for enhancing learning in mammals by peripheral administration of an amount of BA sufficient to induce LTP in the brains of such mammals. As used herein a "therapeutic amount" of BA, or an analog or derivative thereof, is an amount calculated to achieve and maintain a blood level in the brain of a human or animal over the period of time desired sufficient to enhance LTP These amounts vary with the potency of each analog or derivative, the amount required for the desired therapeutic or other effect, the rate of elimination or breakdown of the substance by the body once it has entered the bloodstream, the blood-brain barrier transport mechanism involved in transport of the drug into the brain, and the amount of BA or its analog or derivative in the formulation.

One skilled in the art of treatment of the conditions described herein will know how to titrate the dosage to achieve the desired therapeutic effect. In accordance with conventional prudent formulating practices, a dosage near the lower end of the useful range of a particular agent is usually employed initially and the dosage increased or decreased as indicated from the observed response, as in the routine procedure of the physician. In general, however, the amount of the BA, its analog or derivatives, is in the range from about 1.0 to 15.0, preferably 3.0 to 10.0 mg/kg of body weight of the subject to be treated for enhanced learning and memory retention in accordance with this invention.

Preferably and conveniently, the combined or single drug is administered to the subject to be treated by injection, for instance, intravenously or intraperitoneally in combination with a physiologically acceptable carrier. The carrier may comprise any conventional diluting agent for injections such as those described in Remington's "Pharmaceutical Sciences," 17th Edition (Mack Publishing Co., Pennsylvania), the disclosure of which is incorporated by reference. For instance, the BA can be dissolved in or suspended in an aqueous or nonaqueous sterile vehicle that meets the test for pyrogenicity, such as sterile water or sterile aqueous solutions of electrolytes and/or dextrose. One skilled in the art can readily provide additional suitable vehicles for the preparation and administration of therapeutic dosages of the drugs disclosed herein.

The following examples illustrate the manner in which the invention can be practiced. It is understood, however, that the examples are for the purpose of illustration and the invention is not to be regarded as limited to any of the specific materials or conditions therein.

EXAMPLE 1

Transverse slices (500 µm) were cut from the hippocampi of 4–8 week-old rats (or Guinea pigs weighing 300–400 g), submerged, and continuously perfused at 2–3 ml/min with oxygenated artificial cerebrospinal fluid (10 mM NaCl; 5 mM KCl; 1.3 mM $NaH_2PO_4$; 1.9 mM $MgSO_4$.7 $H_2O$; 22 mM $NaHCO_3$) at 30° C. Excitatory post-synaptic potentials were elicited every 5 seconds by stimulation of Schaffer collateral/commissural fibers with bipolar tungsten stimulating electrodes. Stimulation and recording electrodes were placed as shown in FIG. 1A into the pyramidal cell layer of CA1 region and the stratum radiatum for extracellular recordings of the) population spike (PS) and field excitatory postsynaptic potential (EPSP), respectively. A bipolar stimulation electrode positioned in the stratum radiatum was used to stimulate Schaffer collateral/commissural fibers.

PS were recorded from the CA1 pyramidal cell layer before and after BA (0.05–0.5 µg/ml; MW=280.37) application with glass microelectrodes filled with the artificial cerebrospinal fluid. A stock solution of BA in methanol (1 mg/ml) was diluted with oxygenated artificial cerebrospinal fluid and applied to the hippocampal slices at 2–3 ml/min for 2 to 10 minutes. To evaluate the effect of BA, the PS amplitude and slope of EPSP was monitored before and after application of BA.

As shown in FIG. 1B, PS were recorded before and at 150 minutes after application of BA in a concentration of 0.1 µg/ml. As shown in FIG. 1C, field EPSPs were recorded before and 150 minutes after application of BA in a concentration of 0.1 µg/ml. After induction of LTP the amplitude and the slope of the field EPSP increase. Thus, to evaluate the effect of BA, the slope of the EPSP was measured as indicated in the control record.

The BA-induced potentiation lasted for several hours or even longer. The degrees of BA-induced potentiation in individual slices varied largely, probably due to differences in conditions of hippocampus slices, drug concentrations, and/or duration of drug application

EXAMPLE 2

Figure 2B:
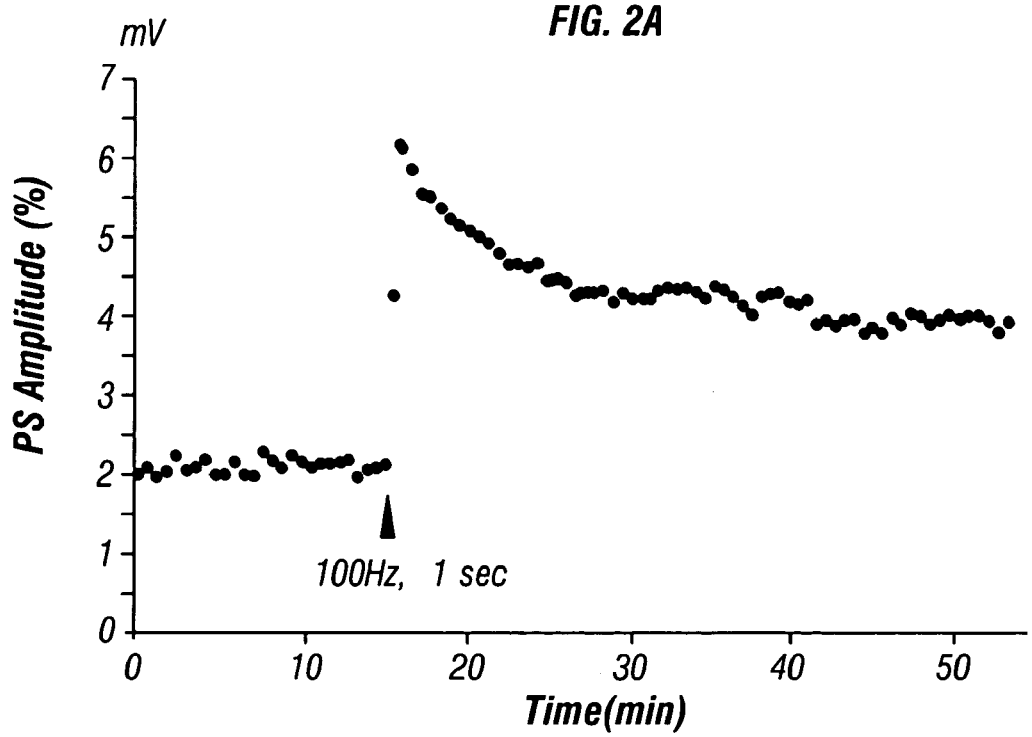
FIG. 2B is a graph showing the time course of the changes in amplitude of the PS recorded in a slice of hippocampal tissue upon administration of tetanus (electric shock) at t=15 minutes, as indicated by the arrowhead.

Studies were conducted to determine the time course of induction of LTP by BA in hippocampal tissue. The amplitude of PS was recorded in a several control hippocampal slices as shown in FIG. 2A. Fluctuations of PS amplitude were within ±20% of baseline during the recording. Upon application of tetanus of 100 Hz for 1 sec at t=15, the amplitudes of PS recorded increased from about 2 mV to about 6 mV (FIG. 2B). In tetanic-induced LTP, the PS amplitude increased immediately after tetanus of 100 Hz for one second and reached a plateau level within several minutes which was higher than that before tetanus.

Figure 2C:
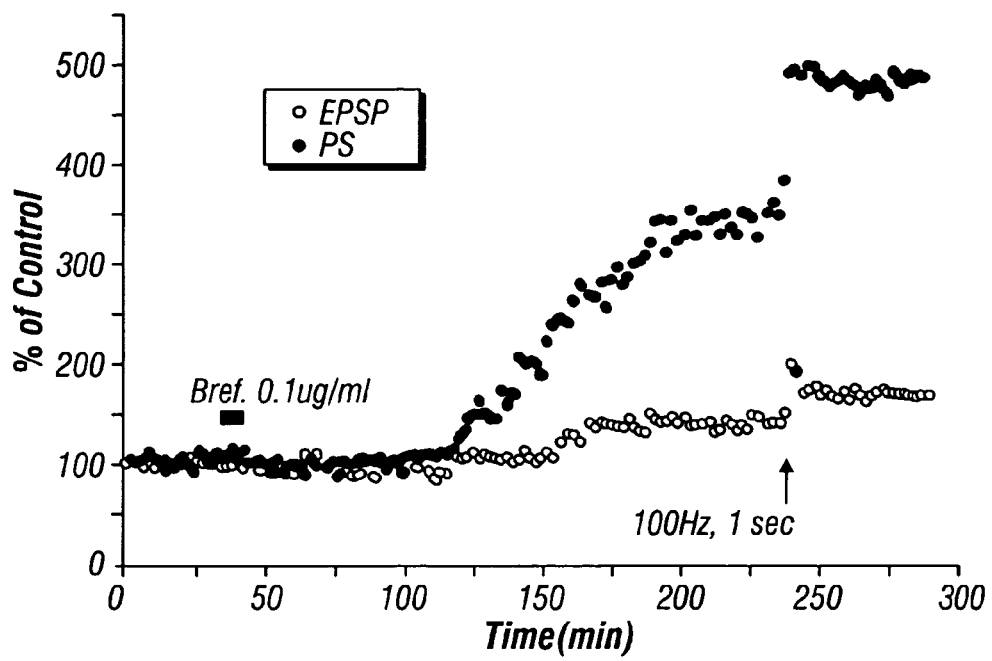
FIG. 2C is a graph showing the time course of the changes in amplitude of the PS and the slope of the field EPSP recorded in a hippocampal slice upon administration of BA. After induction of LTP, tetanus of 100 Hz for one second applied at t=240 minutes caused an additional increase in the amplitude of PS and the slope of the field EPSP, indicating additional LTP. The slope of the field EPSP was measured as indicated by the arrow in FIG. 1C.

As shown in FIG. 2C, when BA was administered to hippocampal tissue at t=50 minutes the PS amplitude and slope of EPSP began to increase approximately 60 minutes after BA application at t=10 minutes. About a four-fold increase (400% that of the control slice) in PS occurred by t=240 minutes, and a small increase in the slope of the field EPSP was observed. Upon administration of tetanus of 100 Hz for 1 second at about t=240 to this slice of hippocampal tissue in which LTP had already been induced by BA, a further increase in PS and slope of the field EPSP was observed. Figure shown is a representative result. Similar results were obtained from over 30 slices.

EXAMPLE 3

Figure 3:
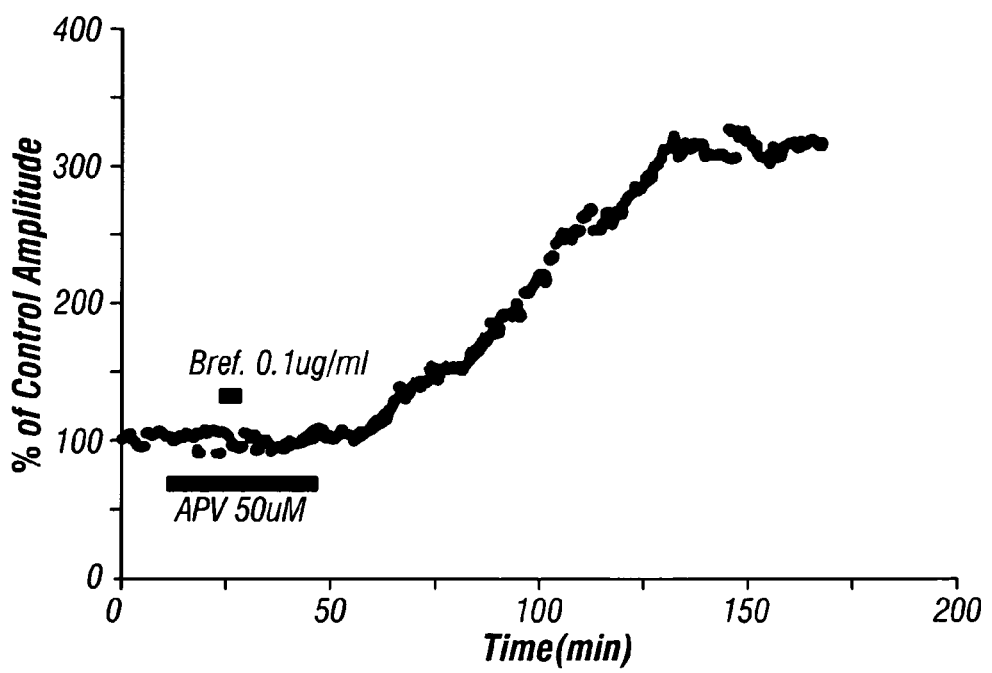
FIG. 3 is a graph showing the results of recordings in a hippocampal slice administered a N-methyl-D-aspartate (NMDA) receptor blocker prior to and during administration of BA (0.1 µg/ml). The results indicate induction of LTP without the involvement of NMDA receptors.

An experiment was conducted to measure BA-induced (0.1 µg/ml) increase in LTP in a hippocampal slice prepared as in Example 1 in the presence of APV, a N-methyl-D-aspartate (NMDA) receptor blocker. Administration of a 50 µM solution of APV was commenced at t=10 minutes and continued until t=50 minutes. As shown in FIG. 3, administration of 0.1 µg/ml of BA in the artificial cerebral spinal fluid of Example 1 at about t=25 minutes resulted in a three-fold increase in the amplitude of PS over that of the same slice before BA application. This demonstrates NMDA receptor independent induction of LTP by BA.

EXAMPLE 4

Induction of LTP In vivo by Brefeldin A.

Figure 4A:
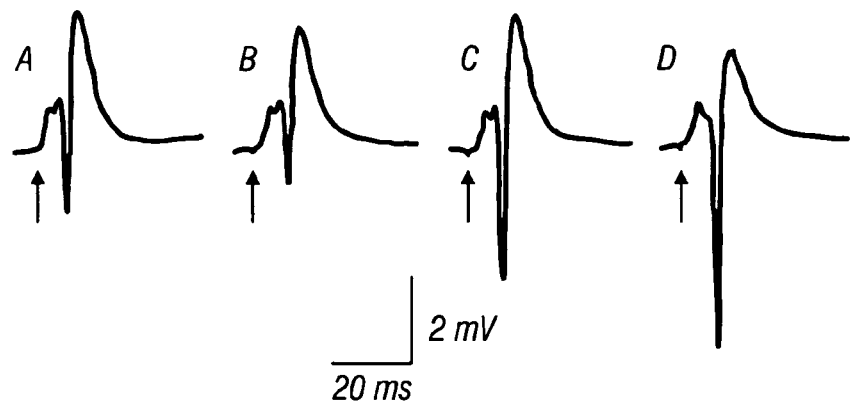
FIG. 4A is a graph showing the results of recordings at time points a, b, c, and d of the PS in the hippocampus of an experimental rat injected intraperitoneally with BA to induce LTP.
Figure 4B:
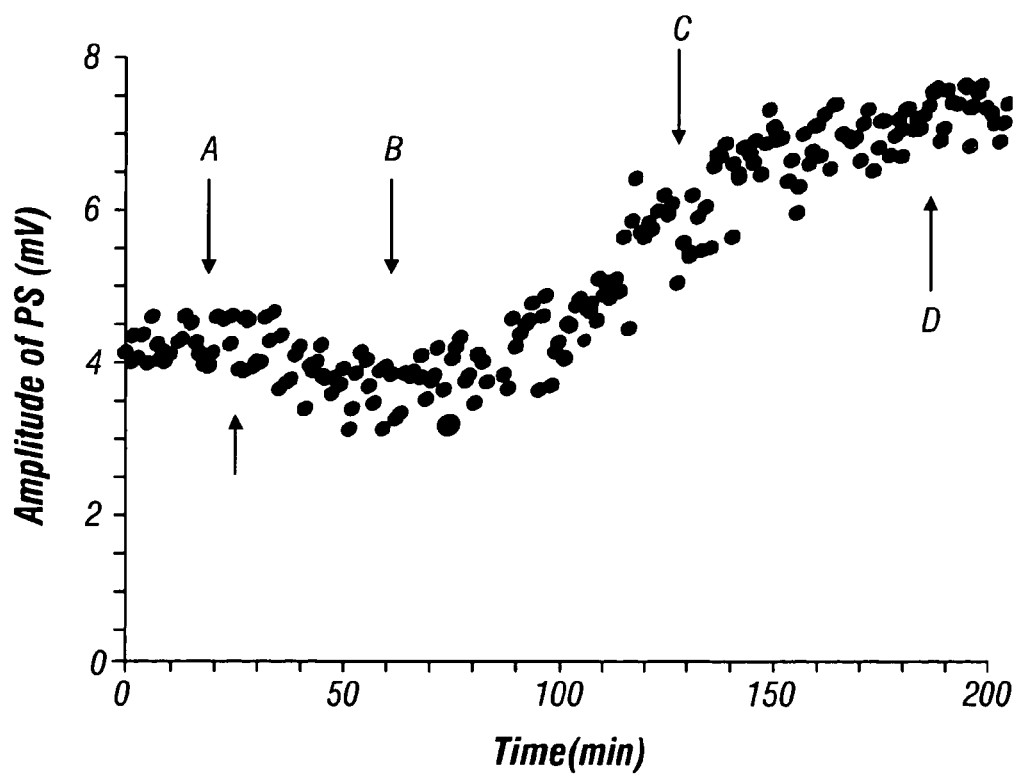
FIG. 4B is a graph showing the time course of the change in population spike amplitude induced in the hippocampus of an experimental rat injected intraperitoneally with BA (3 mg/kg) to induce LTP at the time point indicated by the arrow in bold.
Figure 4C:
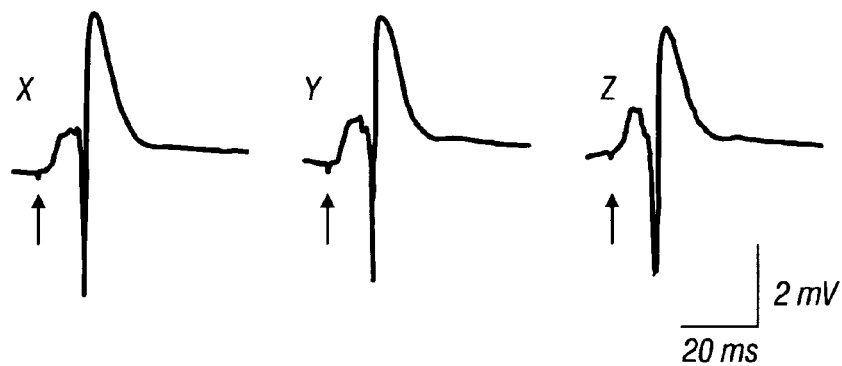
FIG. 4C is a graph showing the results of recordings at time points x, y and z of the PS in the hippocampus of a control rat injected peripherally with saline vehicle.
Figure 4D:
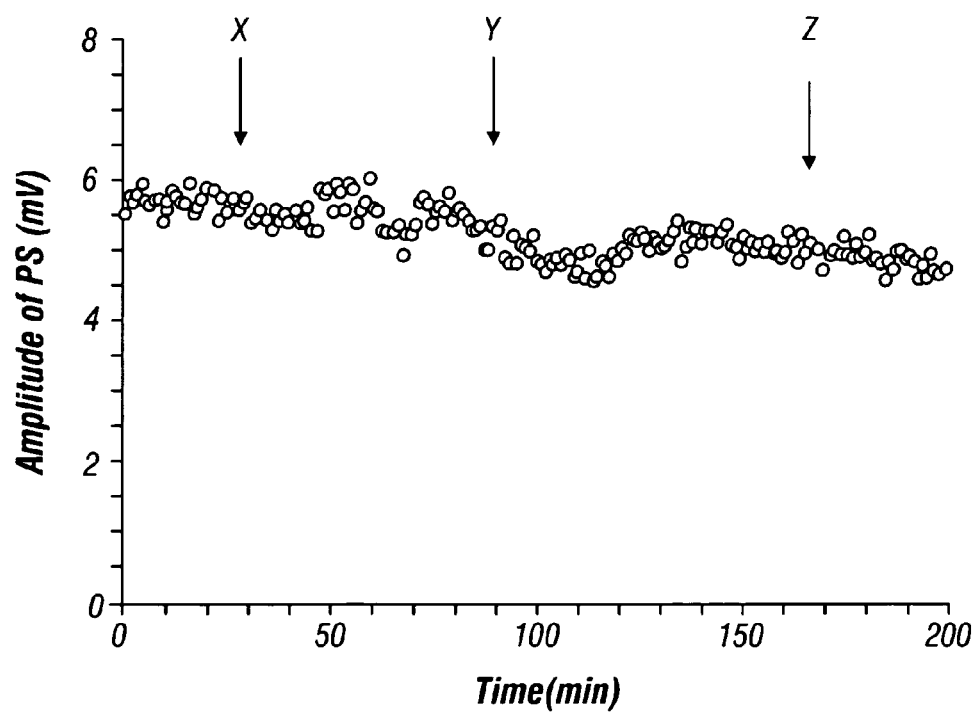
FIG. 4D is a graph showing the time course of the change in population spike amplitude in the hippocampus of a control rat injected peripherally with saline vehicle at the time point indicated by the arrow in bold.

In this experiment LTP was induced in the CA1 area of the hippocampus of anesthetized male Sprague Dawley (250–275 g) rats aged about two months after peripheral administration of BA, showing that BA crosses the blood brain barrier in sufficient concentration to induce LTP. Recordings of the PS (FIG. 4A) and the time courses of the change in PS amplitude (FIGS. 4B) were made just before and at intervals after intraperitoneal administration of BA at a concentration of 3 mg/kg. FIGS. 4C and 4D show the recordings of the PS and the time course of the change in PS amplitude, respectively, from a control rat which received injection the saline vehicle without BA. Similar results were obtained with four additional animals. As can be seen by comparing the results summarized in FIGS. 4A and 4D, the rat receiving peripheral BA showed a 200% increase in the amplitude of PS over the course of about 170 minutes, while the amplitude of the PS in the control rat declined slightly.

EXAMPLE 5

Effect of BA Upon Learning of Inhibitory Avoidance.

Figure 5:
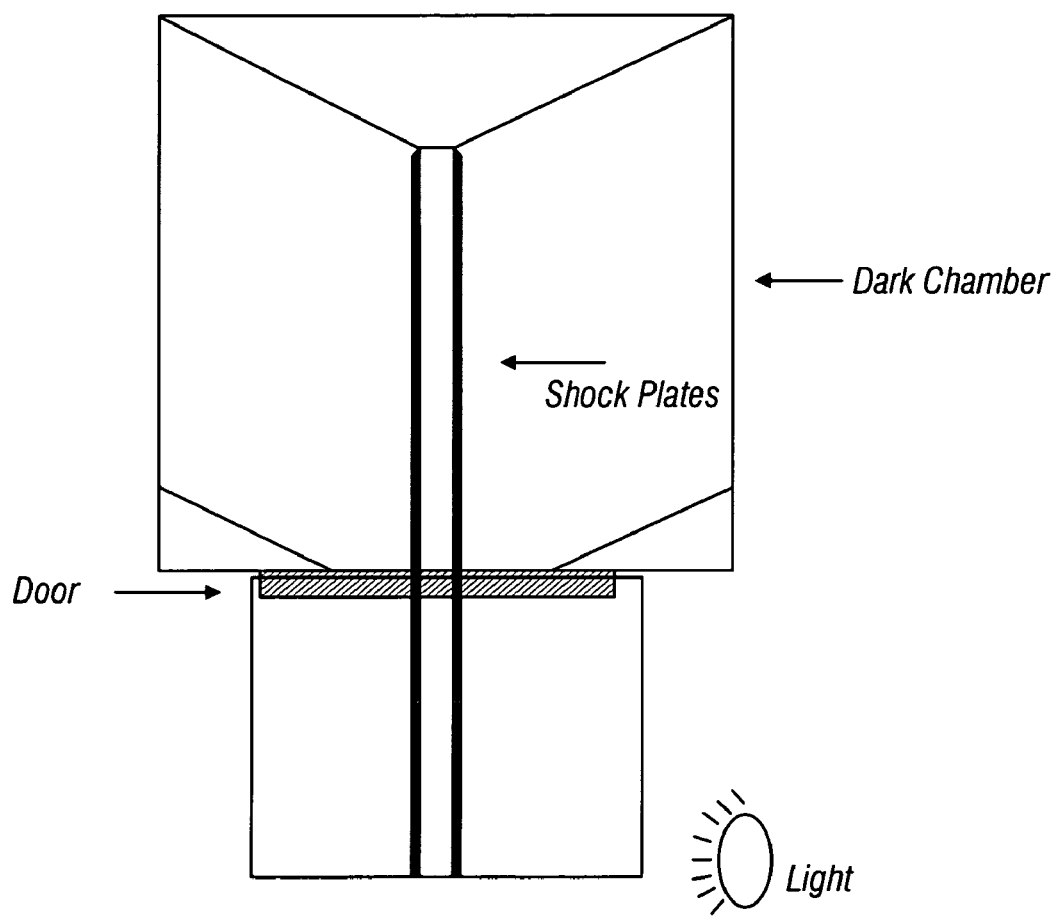
FIG. 5 is a schematic drawing illustrating the apparatus used for testing acquisition of inhibitory avoidance tasks in mice.
Figure 6A:
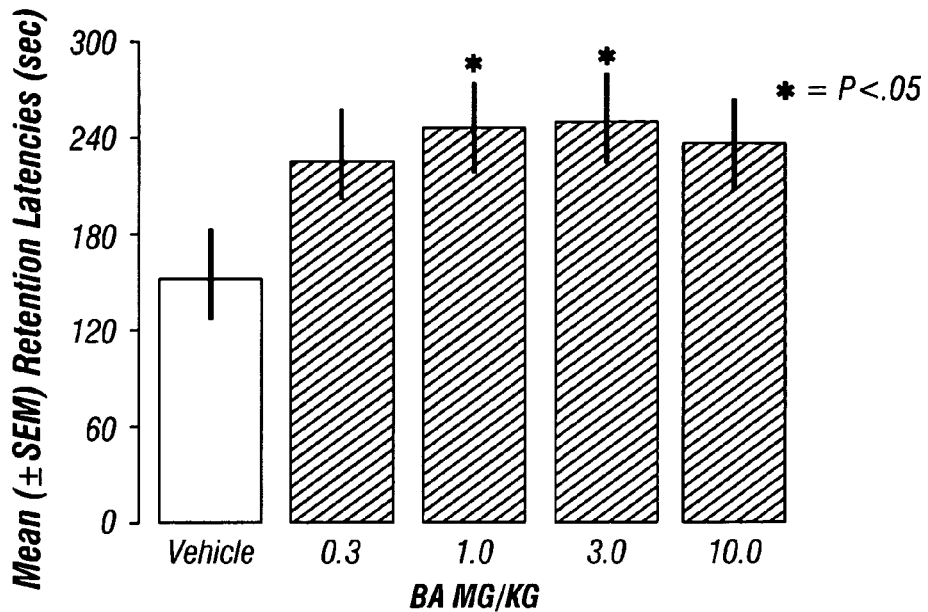
FIG. 6A is a dose-response histogram showing mean retention latencies in seconds of experimental mice administered BA two hours before training in acquisition of inhibitory avoidance tasks.
Figure 6B:
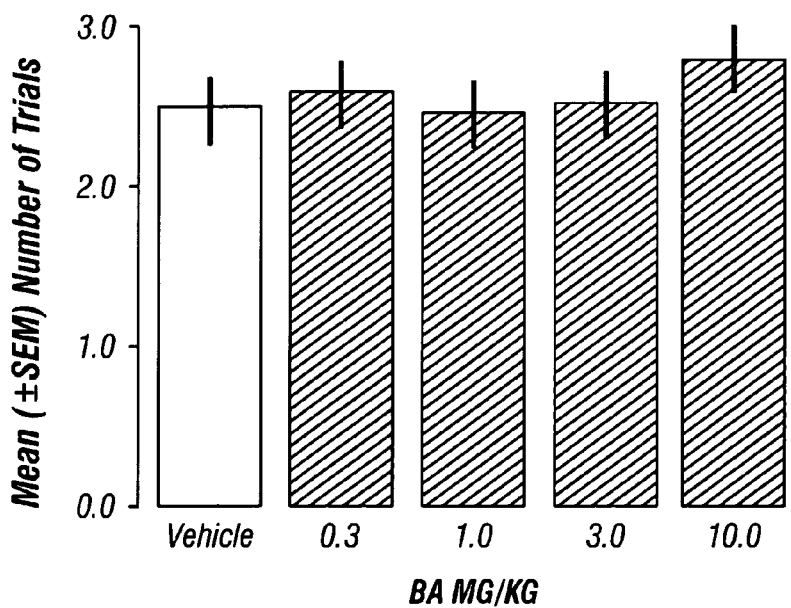
FIG. 6B is a histogram showing the mean number of trials for acquisition of inhibitory avoidance tasks in test mice administered BA two hours before training sessions.

For testing of learning in an inhibitory avoidance (IA) task, five groups of 12 male, CD-1 mice (Charles River Labs, Wilmington, Mass.) (27–30 g, 3–4 weeks) were tested to determine the effect upon learning of peripheral administration two hours before training sessions of either saline vehicle (3% ethanol in physiological saline) (as control) or 0.3, 1.0, 3.0, or 10.0 mg/kg of BA in the saline vehicle. The test apparatus used was a divided lucite box illustrated schematically in FIG. 5. One side of the box was illuminated, while the other side, which is slightly larger than the lighted side remained dark. In the dark arm the flood has two plates separated by less than a centimeter connected to a positive and a negative termini so as to deliver a shock of 0.6 mA through the floor bars of the box in the dark compartment to the foot of the animal.

Animals were injected either 7 days or 120 minutes prior to training, or 120 min. post training and tested 48 h. later. For training the mouse was placed facing the experimenter (away from the door to the dark chamber) in the lighted side of the box. The door dividing the two chambers was lifted, and the time transpiring before the mouse entered the dark chamber (the latency) was measured. Upon receiving the mild shock, the mouse returned to the lighted side, at which time the clock was reset. Then a second latency was measured and if the latency was greater than 60 seconds but less than 300 seconds it was recorded. All animals were required to show a minimum of 60 seconds latency to enter the dark chamber, at which point they were deemed to have acquired the inhibitory avoidance task (acquisition).

Forty eight hours after training, a retention test was conducted in which the animal was placed in the illuminated chamber and the latency to enter the dark chamber was recorded. All experiments were run as double blind studies. Statistical significance was calculated according to analysis of variance (ANOVA) and Mann-Whitney non-parametric testing.

As shown in FIG. 5A, mice treated with 1.0 and with 3.0 mg/kg doses experienced statistically significant increase (p(0.05) in mean retention latencies, as compared with those of control mice, indicating that these animals stayed in the illuminated chamber longer before reentering the dark chamber, where they had previously experienced shock, than did control mice. Increased retention latencies are indicative of increased memory retention.

The mean number of trials required by each group to reach the 60 second criterion level (designated acquisition) is shown in FIG. 5B. There was no significant difference in acquisition among the groups, indicating that the drug does not affect the initial achievement of the 60 second latency.

EXAMPLE 6

Acquisition of Reversal Discrimination in a Y Maze Task.

Figure 7:
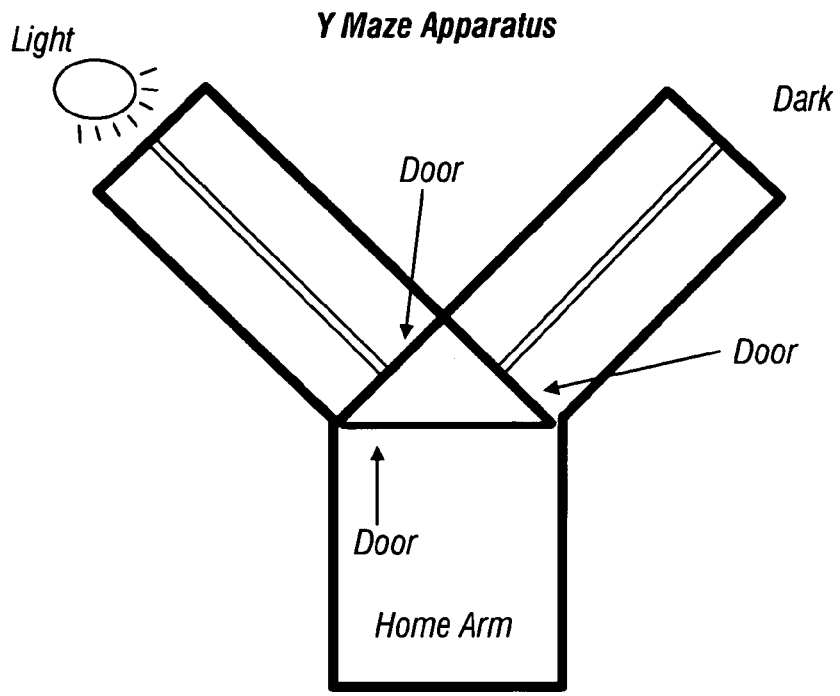
FIG. 7 is a schematic drawing illustrating the Y maze apparatus used for testing inhibitory avoidance in mice.

The Y maze apparatus as illustrated by FIG. 7 consists of a lucite chamber with three arms, each approximately one foot long. The floors of the arms were similar to those of the IA apparatus of Example 5, having two plates separated by less than a centimeter connected to a positive and a negative terminal so as to deliver a 0.35 mA shock to the foot of the test animal. The Y maze is used to test the animal's capacity to remember which of the two arms delivered a shock during the preliminary learning phase. Therefore, during the testing phase the safe arm is reversed from the one that was safe during the learning phase. The more the animal remembers from the learning phase, the more errors it will make during the test phase. Consequently, a high error score indicates learning of the task.

The training phase of the Y maze discrimination reversal task was as follows. Animals were placed in a three arm lucite Y maze apparatus, with each arm separated by a sliding door (FIG. 7). The left arm was illuminated during testing as during training, while the center arm and the right arm remained dark. Animals were placed in the darkened center (start) arm (at the base of the Y); after 10 seconds, a footshock (0.35 mA, 60 Hz) was delivered to the start arm and to the intersection of all three arms, but not to the illuminated arm until the animal entered the lighted arm. Mice that failed to enter the lighted arm within 60 seconds were removed and placed again into the start arm. Those that had fully entered the illuminated arm were lifted and returned to the start arm. The interval between training trials was 40 seconds. The final stage of training required that, when given the choice between the lighted and dark arms, the mice successfully chose the lighted arm three consecutive times (the criterion). All mice were then subjected to a forced entry into the dark arm where they received a 5 second footshock to ensure that all animals experienced footshock in the dark arm.

Figure 8:
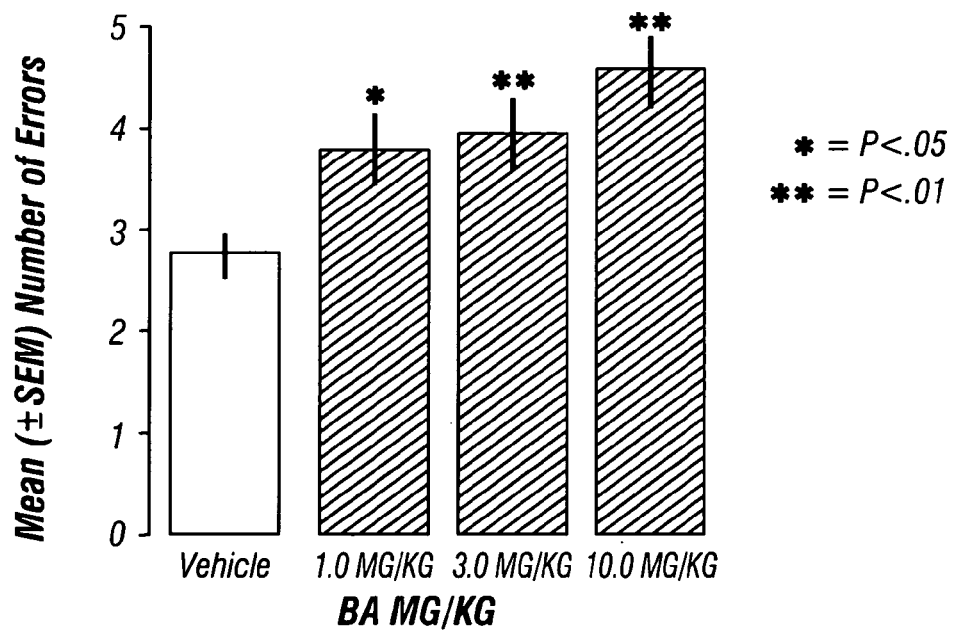
FIG. 8 is a dose-response histogram showing the mean number of errors on a reversal discrimination task as a function of the dose of BA administered two hours prior to training in the Y maze illustrated in FIG. 7. The control group of 12 mice was administered saline (vehicle). The higher the mean number of errors, the greater is the indication of acquisition of the task. All three groups of mice (12 mice per group) receiving the BA exhibited a higher mean number of errors than the control group did.

Testing was conducted 48 hours later, but with the dark arm as the safe arm and the illuminated arm providing a foot shock. All mice were given six test trials. Records were made of the first arm chosen by the animal during testing (L=lit or D=dark) and of the latency period to reach the dark (safe) arm. The number of errors in six trials was recorded. As shown by the data in FIG. 8, administration of BA in the saline vehicle described above to three groups of mice (n=12) at a dosage of 1.0, 3.0 or 10.0 mg/kg of body weight all resulted in a statistically significant increase of errors over that of the control group (n=24), which received administration only of the saline vehicle (3% ethanol in physiological saline), indicating that the drug facilitates memory for this task.

EXAMPLE 7

Figure 9:
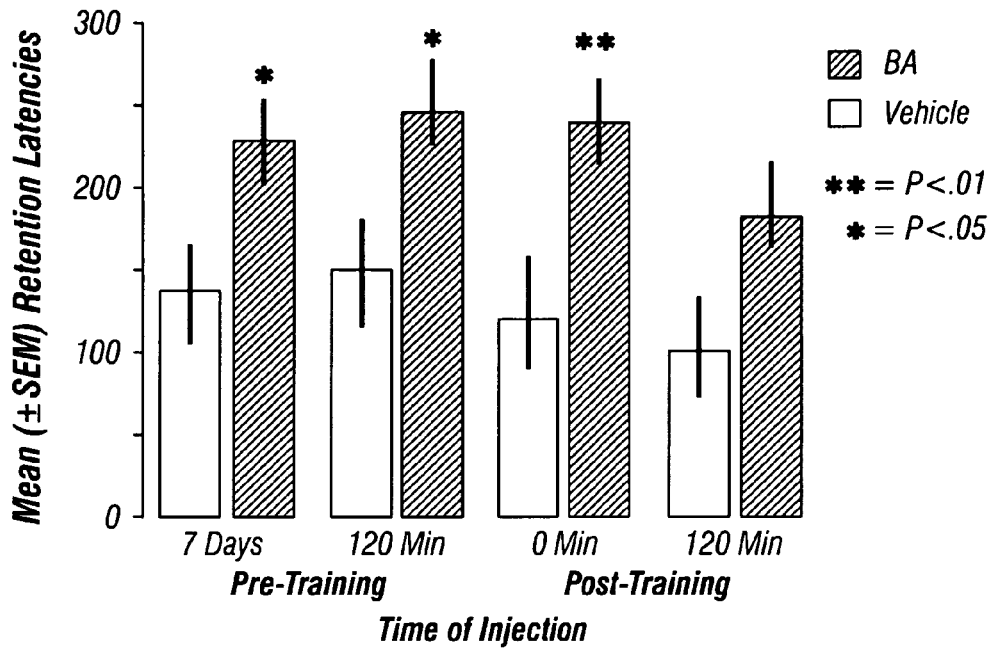
FIG. 9 is a time course histogram showing the mean retention latencies in groups of mice (n=12) trained in the apparatus illustrated in FIG. 5 that have been injected intraperitoneally with BA 7 days or 120 minutes before training sessions, immediately before training, or two hours after training sessions.

To determine the retention latencies of BA, the drug was injected peripherally into groups of mice (n=12) at a dosage of 3 mg/kg intraperitoneally at various time intervals prior to or following training and performance of the acquired learning task described in Example 6 of this application. Four sets of control and test groups of mice (12 mice per group) were injected with BA at a dosage of 3mg/kg of body weight 7 days prior to training, 120 minutes prior to training, immediately prior to training, or 120 minutes after training. As shown by the results summarized in FIG. 9, the mean retention latencies in test animals were significantly higher than control when the drug was injected 7 days prior to training, 2 hours prior to training, and immediately post-training. However, injection of BA two hours post training did not result in an increase in retention latency over that of the control group. No adverse health effects that could be attributed to the administration of BA were observed in the test mice.

EXAMPLE 8

Figure 10:
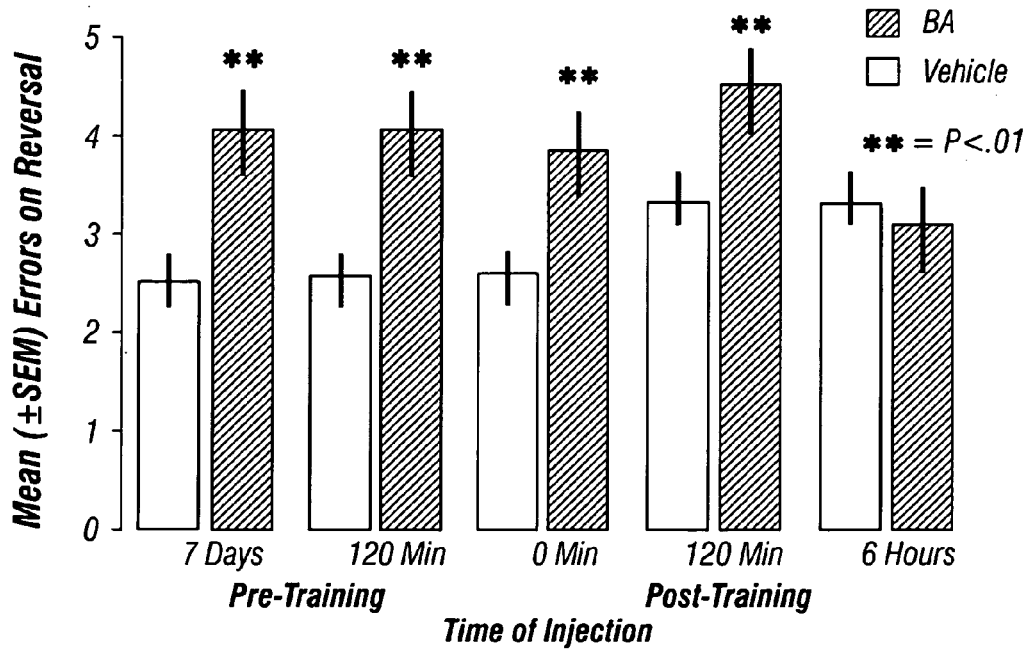
FIG. 10 is a time course histogram comparing the mean retention latencies in groups of mice (n=12) trained in the Y maze apparatus illustrated in FIG. 7 that have been injected intraperitoneally with BA or vehicle either 7 days or 120 minutes before training sessions, immediately before training, or two or six hours after training sessions.

To determine the retention latencies of BA, the drug was injected intraperitoneally into groups of mice at a dosage of 3 mg/kg at various time intervals prior to or following training and performance of the acquired learning in the Y maze task described in Example 7 of this application. Four sets of control and test groups of mice (12 mice per group) were injected with BA at a dosage of 3 mg/kg of body weight 7 days prior to training, 120 minutes prior to training, immediately post training, or 120 minutes after training. As shown by the results summarized in FIG. 10, the number of errors on reversal in test animals was significantly higher than in the parallel control group when the drug was injected up to 7 days prior to training and up to 2 hours post training. However, injection of BA six hours post training did not result in an increase in the number of errors over that of the control group. No adverse health effects that could be attributed to the administration of BA were observed in the test mice.

The foregoing description of the invention is exemplary for purposes of illustration and explanation. It should be understood that various modifications can be made without departing from the spirit and scope of the invention. Accordingly, the following claims are intended to be interpreted to embrace all such modifications.

The invention claimed is:

1. A method of enhancing learning in a mammal comprising administering to the mammal a compound having a formula selected from the group consisting of:

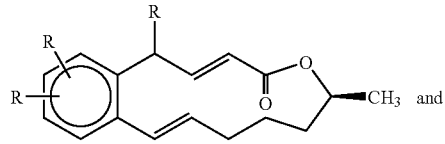

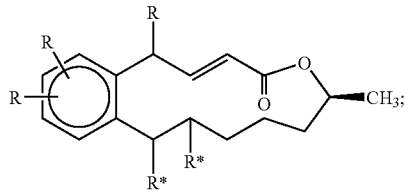

wherein each R is independently selected from —OH, —OR$^1$, —SH, —SR$^1$, —NR$^2$R$^2$, and a carbonyl oxygen; and R* is hydrogen or —OH; and wherein R$^1$ is a $C_1$ to $C_4$ alkyl; and R$^2$ is a $C_1$ to $C_4$ alkyl.

2. The method of claim 1, wherein the amount of the compound administered is from about 1.0 to 15.0 mg/kg of body weight.

3. The method of claim 1, wherein the amount of the compound administered is from about 3.0 to 10.0 mg/kg of body weight.

4. The method of claim 1, wherein the mammal has a healthy brain.

5. The method of claim 1, wherein the compound is administered up to seven days before the learning.

6. The method of claim 1, wherein the compound is administered up to two hours after the learning.

7. A method for treating memory dysfunction in a mammal comprising administering to the mammal a compound having a formula selected from the group consisting of:

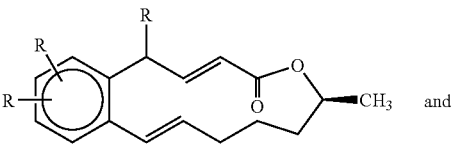

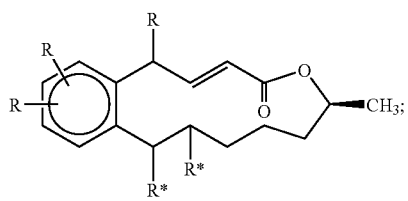

wherein each R is independently selected from —OH, —OR$^1$, —SH, —SR$^1$, —NR$^2$R$^2$, and a carbonyl oxygen; and R* is hydrogen or —OH; and wherein R$^1$ is a $C_1$ to $C_4$ alkyl; and R$^2$ is a $C_1$ to $C_4$ alkyl.

8. The method of claim 7, wherein the memory dysfunction is associated with a decrease in the efficiency of synaptic transmission or loss of functioning synapses in the hippocampus.

9. The method of claim 7, wherein the amount of the compound is from about 1.0 to 15.0 mg/kg of body weight.

10. The method of claim 9, wherein the amount of the compound is from about 3.0 to 10.0 mg/kg of body weight.

11. A composition comprising a physiologically acceptable carrier and a compound having a formula selected from the group consisting of:

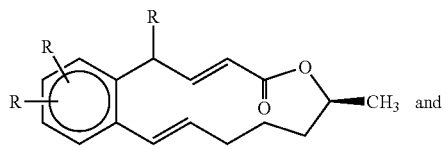

and

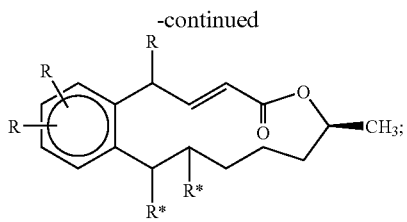

wherein each R is independently selected from —OH, —OR$^1$, —SH, —SR$^1$, —NR$^2$R$^2$, and a carbonyl oxygen; and R* is hydrogen or —OH; and wherein R$^1$ is a $C_1$ to $C_4$ alkyl; and R is a $C_1$ to $C_4$ alkyl.

12. The composition of claim 11, wherein the physiologically acceptable carrier is an aqueous or non-aqueous sterile vehicle.

* * * * *